United States Patent
Kirkhope (10) Patent No.: US 9,637,981 B2
(45) Date of Patent: May 2, 2017

(54) WELLBORE COMPONENT LIFE MONITORING SYSTEM

(71) Applicant: Halliburton Energy Services, Inc., Houston, TX (US)

(72) Inventor: Kennedy J. Kirkhope, Alberta (CA)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/425,594

(22) PCT Filed: Jul. 11, 2013

(86) PCT No.: PCT/US2013/050078
§ 371 (c)(1),
(2) Date: Mar. 3, 2015

(87) PCT Pub. No.: WO2015/005923
PCT Pub. Date: Jan. 15, 2015

(65) Prior Publication Data
US 2015/0226013 A1    Aug. 13, 2015

(51) Int. Cl.
*E21B 12/02* (2006.01)
*G01N 3/56* (2006.01)

(52) U.S. Cl.
CPC .............. *E21B 12/02* (2013.01); *G01N 3/56* (2013.01)

(58) Field of Classification Search
CPC .................................. E21B 12/02; G01N 3/56
USPC ........................................................... 702/6
See application file for complete search history.

(56) References Cited

U.S. PATENT DOCUMENTS

| | | | |
|---|---|---|---|
| 4,608,861 A | 9/1986 | Wachtler et al. |
| 4,811,597 A | 3/1989 | Hebel |
| 5,321,981 A | 6/1994 | Macpherson |
| 5,361,846 A | 11/1994 | Carlin et al. |
| 5,853,199 A | 12/1998 | Wilson |
| 6,065,332 A | 5/2000 | Dominick |
| 6,722,450 B2 | 4/2004 | Schultz et al. |
| 6,817,425 B2 | 11/2004 | Schultz et al. |
| 7,082,821 B2 | 8/2006 | Chen et al. |
| 7,140,452 B2 | 11/2006 | Hutchinson |
| 7,357,197 B2 | 4/2008 | Schultz et al. |
| 7,757,552 B2 | 7/2010 | Bogath et al. |
| 8,014,987 B2 | 9/2011 | Pabon et al. |
| 8,214,188 B2 | 7/2012 | Bailey et al. |
| 2005/0133260 A1 | 6/2005 | Singh et al. |

(Continued)

OTHER PUBLICATIONS

Authorized Officer Jong Kyung Lee, PCT International Search Report and Written Opinion of the International Searching Authority, PCT/US2013/050078, Apr. 14, 2014, 15 pages.

(Continued)

*Primary Examiner* — Ricky Ngon
(74) *Attorney, Agent, or Firm* — John W. Wustenberg; Parker Justiss, P.C.

(57) ABSTRACT

Wellbore component life monitoring system. A life of a component in a wellbore can be monitored by periodically receiving a load value of a load while the load is being applied to a component in a wellbore. While the load is being applied to the component in the wellbore, a fatigue on the component caused by the load can be periodically determined based, at least in part, on the periodically received load value.

22 Claims, 4 Drawing Sheets

(56) References Cited

U.S. PATENT DOCUMENTS

| | | |
|---|---|---|
| 2008/0319720 A1* | 12/2008 | Ellis .................... F16L 15/004 703/2 |
| 2010/0100337 A1 | 4/2010 | Vichare et al. |
| 2010/0212961 A1* | 8/2010 | Teodorescu ............ E21B 12/02 175/39 |
| 2011/0186353 A1* | 8/2011 | Turner ................ G05B 13/048 175/40 |
| 2012/0016589 A1 | 1/2012 | Li et al. |
| 2013/0113491 A1 | 5/2013 | Rodney |
| 2013/0153295 A1 | 6/2013 | Rodgers et al. |

OTHER PUBLICATIONS

PCT International Preliminary Report on Patentability, PCT/US2013/050078, Jan. 21, 2016, 12 pages.

Australian Government IP Australia, Patent Examination Report No. 1, Australian Application No. 2013393827, Mar. 29, 2016, 3 pages.

* cited by examiner

WELLBORE COMPONENT LIFE MONITORING SYSTEM

CLAIM OF PRIORITY

This application is a 371 U.S. National Phase Application of and claims the benefit of priority to PCT International Application No. PCT/US2013/050078, filed on Jul. 13, 2013, the entire contents of which are hereby incorporated by reference.

TECHNICAL FIELD

This disclosure relates to components, for example, drilling components, used in wellbores.

BACKGROUND

Wellbore drilling is a process of drilling a hole in the ground for the extraction of one or more natural resources, e.g., petroleum, brine, natural gas, ground water, or combinations of them. Wellbores can also be drilled to inject a fluid from a surface to a subsurface reservoir or to evaluate or monitor subsurface formations. Components used in wellbores, e.g., wellbore drilling tools, can be subjected to cyclic loads due to, e.g., repeated loadings or vibration or combinations of them. Such loads can lead to fatigue, cumulative damage, and eventually failure of the component. A life of a component used in a wellbore can depend upon factors including the load applied to the component, a rate at which and a duration for which the load is applied, physical properties of the formation(s) in which the component is operated, and other factors. Knowledge of the load applied to the component can enable monitoring a fatigue on the component and a life of the component.

DESCRIPTION OF DRAWINGS

Like reference symbols in the various drawings indicate like elements.

DETAILED DESCRIPTION

This disclosure relates to monitoring lives of components operated in wellbores, for example, for drilling the wellbores. Such components, e.g., drilling tools, encounter loads, e.g., weight on bit, torque, bending moment, and other loads, when operated downhole, and, consequently, are susceptible to fatigue caused by the loads. Knowing a life of a component can be useful to a drilling rig operator who operates the tool. A life of a component can be anticipated, e.g., by performing endurance testing under laboratory conditions and comparing the obtained data with known field data. For example, a drilling tool can be subjected to cyclic loads under laboratory conditions. A method of calculating the fatigue of the drilling tool under the laboratory conditions can be calibrated based on performance and life expectancy determined and stored for identical or substantially similar tools that have been used in the other wellbores in the past.

However, conditions under which the component is subjected to loads may not match field conditions, e.g., wellbore conditions, in which the component is operated. Even if laboratory conditions can be simulated to match field conditions, the component may not necessarily be operated under the simulated field conditions at all times. For example, the component may be operated in a first wellbore under a first set of field conditions (such as load applied and time for which the load is applied) and later in a second wellbore under a second set of field conditions. The first wellbore may be different from the second wellbore resulting in the second set of conditions being different from the first set. Consequently, fatigue analysis under laboratory conditions may not be an accurate predictor of the life of a component that is used in different wellbores.

Moreover, under laboratory conditions, it may be difficult or may not be possible to determine a portion of the life of the component that has been consumed due to the fatigue caused by the loads applied to the component while the loads are being applied to the component. For example, loads applied to a drill bit used to drill a wellbore may be analyzed to determine a portion of the life of the component that has been consumed after the wellbore has been drilled and, for example, the drill bit removed from the wellbore. If the portion of the life that has been consumed exceeds the maximum available life of the drill bit while the wellbore is being drilled, then the drill bit may fail. Also, removing the drill bit mid-way through a drilling job to analyze the drill bit's life is not always economically feasible. The inability or difficulty to determine the portion of the life of the component that has been consumed and that is remains while the component is being operated in the wellbore can result in non-productive time and necessitate expensive operations to replace the component should the component fail.

This disclosure describes techniques to monitor a life of a component in a wellbore under actual field conditions, i.e., the wellbore conditions, rather than simulated laboratory conditions. This disclosure also describes techniques to determine a portion of the life of the component consumed due to the fatigue caused by the loads applied to the component while the loads are being applied. In general, the techniques described here can be implemented to determine the fatigue of any component that can suffer fatigue damage. In addition to drill tools, examples of such components can include drive shafts, mud motors, rotary steerable systems, formation evaluation (FE) collars with outserts, i.e., ports drilled through the outside, and other suitable components.

As described below, actual loads applied to the component and the time for which the loads are applied can be periodically recorded. To perform a fatigue analysis, the loads and the time can be provided as input to a fatigue model which can provide a predicted life of the component as an output. Sometimes, the component may not reach its predicted life in a single operation, which means that the component can be reused for one or more additional operations. By recording and providing a load history as input to the fatigue model coupled with a cumulative damage model, the component life can be predicted as part of a condition-based maintenance system in which decisions regarding retiring critical components (e.g., components approaching their predicted lives) prior to downhole failure can be made.

For example, an operator of the technique may know that a component to be operated in a wellbore has 10% remaining life. The life expectancy can be based on a given load case. In this example, the life expectancy can be the maximum specified operating load. If the user knows the anticipated loads are less than the maximum specified, then more than 10% of life may be remaining Based on the wellbore conditions and a past history of similar components, the operator can determine that operating the component in the wellbore will consume 25% of the life of the component. Based on this determination, the operator can determine to not use the component. Alternatively, based on the wellbore conditions and the past history of similar components, the operator can determine that operating the component in the wellbore will consume only 5% of the life of the component. Based on this determination, the operator can determine to use the component even though only 10% of the component's life remains.

As an alternative or in addition to recording the loads, the loads can be reported periodically, for example, in real time, enabling fatigue determination as often as the loads are reported. Such fatigue analysis can allow the drilling rig operator to determine if the loading for a particular operation is higher than anticipated. The comparison can be used to provide an early warning to prevent downhole failure. In sum, the techniques described here can minimize non-productive time, for example, by preventing downhole failures by performing scheduled repairs or replacements (or both) based on periodically performed fatigue analysis of components.

Figure 1:
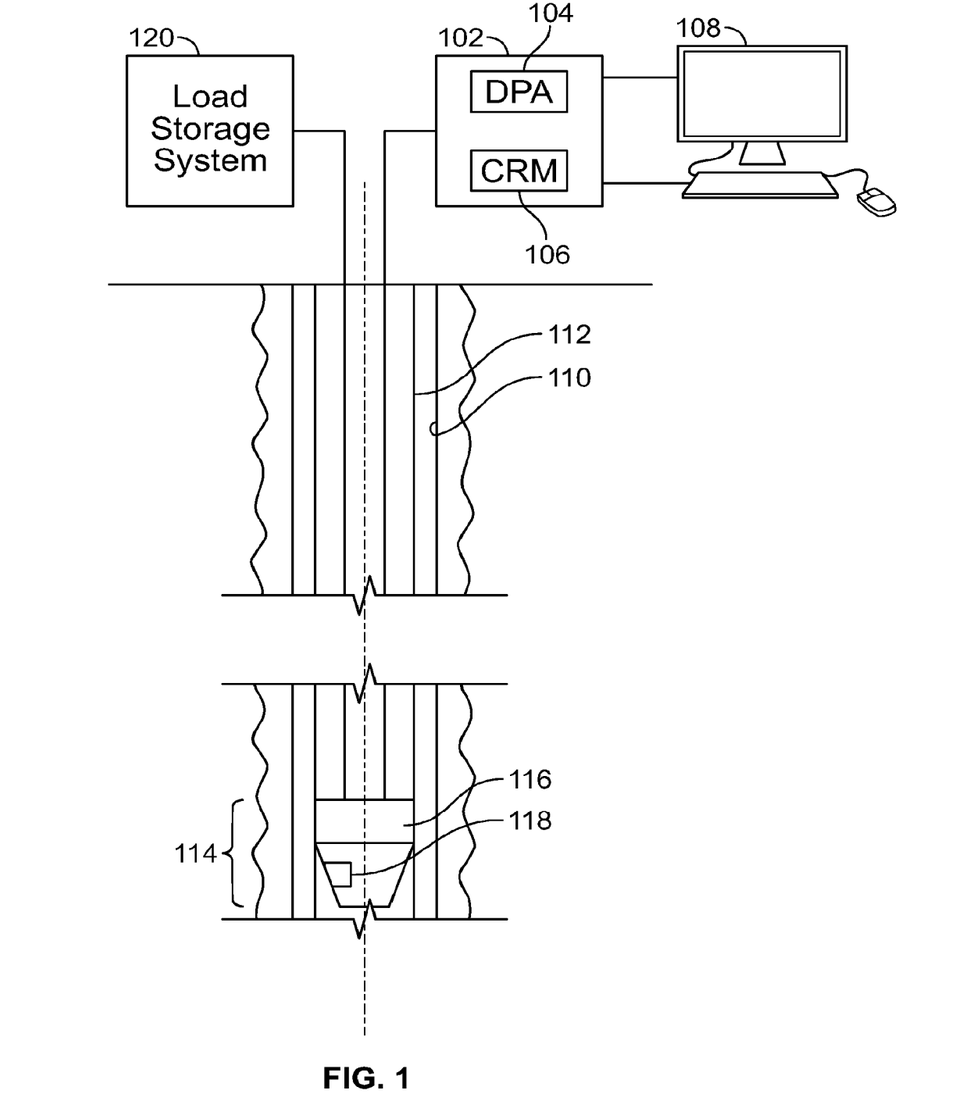
FIG. 1 illustrates an example of a wellbore system connected to a wellbore component life monitoring system.

FIG. 1 illustrates an example of a wellbore system connected to a wellbore component life monitoring system 102. The example wellbore system can include a wellbore 110 that extends from a terranean surface into one or more subterranean zones. A tool string 112 carrying a component, for example, a drilling tool, can be inserted into the wellbore 110. The wellbore 110 can be connected to a wellbore component life monitoring system 102, which can be implemented uphole, e.g., at the surface, as shown in FIG. 1 or downhole.

In some implementations, the monitoring system 102 can be a computer system (for example, a desktop computer, a laptop computer, a tablet computer, a smartphone, a server computer system, or other suitable computer). The monitoring system 102 can include a computer-readable medium 106 storing computer instructions executable by data processing apparatus 104 to perform component life monitoring operations such as those described here. In some implementations, while a load is being applied to a component in the wellbore, the monitoring system 102 can periodically receive load values of the load. While the load is being applied to the component in the wellbore, the monitoring system 102 can periodically determine a fatigue on the component caused by the load based, at least in part, on the periodically received load values.

The monitoring system 102 can be connected to a load measuring system 114 that is connected to the component in the wellbore 110. The load measuring system 114 can periodically measure the load values of the load while the load is being applied to the component, and provide the load values to the monitoring system 102. For example, the load measuring system 114 can include a strain gauge 118 to sense a strain on the component, and a computer system 116 to receive the strain sensed by the strain gauge 118 and transform the strain into the load value (e.g., weight on bit, torque, bending moment) of the load being applied to the component. The load measuring system 114 can similarly be connected to other strain gauges or sensors (or both) disposed anywhere in the wellbore 112. The computer system 116 can be implemented downhole, e.g., in or near the bottom hole assembly, or uphole, e.g., at or near the surface. The load measuring system 114 can measure and provide the loads such that the monitoring system 102 periodically receives the load values of the load while the component is being operated in the wellbore 114. An example load measuring system 114 is the DrillDOC® tool offered by Halliburton Energy Services, Inc. (Houston, Tex.).

The monitoring system 102 can be connected to a load storage system 120, which can store a past history of load values of loads that were applied to the component. The past history of load values can include load values measured during one or more previous operations of the component that are different (e.g., discrete) from the current operation of the component. For example, the component that is being operated in the wellbore 112 can previously have been operated to drill a different wellbore. The load measuring system 114 can have measured load values of loads applied to the component when the component was operated to drill the different wellbore. The past history of load values can, alternatively or in addition, include load values measured for each operation in which the component was run into and out of the wellbore 112, for example, for maintenance.

The load storage system 120 can have received the load values measured by the load measuring system 114 and stored the load values as a past history of load values. The past history of load values can additionally include the wellbore conditions (for example, types of formations) that were drilled using the component during the one or more previous, discrete operations or during one or more runs of the component into and out of the wellbore 112 (or combinations of them). The monitoring system 102 can receive the past history of the load values of the loads that were applied to the component, and periodically determine the fatigue caused by the load based on the past history of the loads. In this manner, the monitoring system 102 can determine a fatigue on the component based not only on load values of loads while the loads are being applied to the component but also on load values of past loads that have previously been applied to the component. Techniques for doing so and for providing the fatigue in real time are described below with reference to FIGS. 2 and 3.

Figure 2:
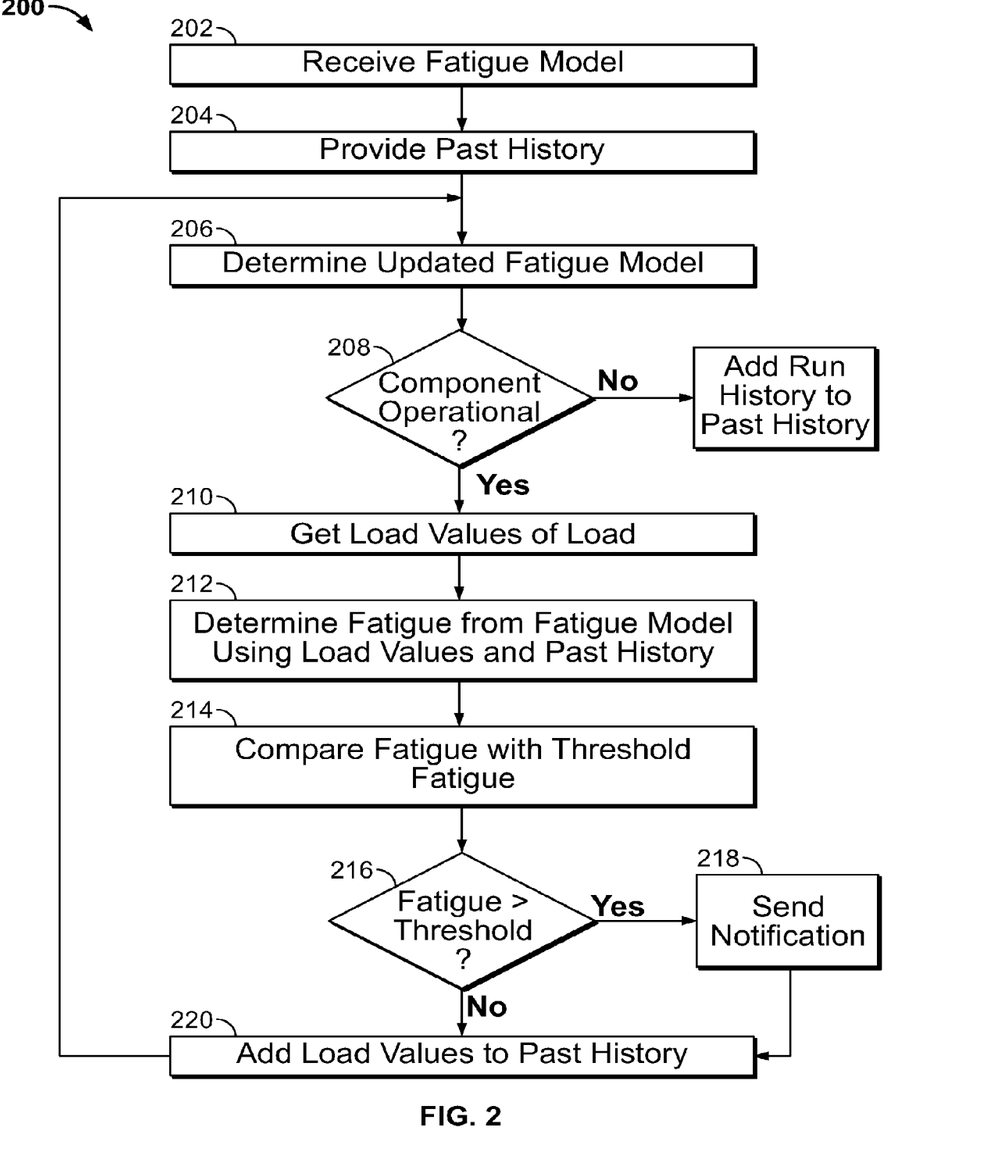
FIG. 2 illustrates a flowchart of an example process for monitoring a life of a component in the wellbore of FIG. 1.

FIG. 2 illustrates a flowchart of an example process 200 for monitoring a life of a component in the wellbore of FIG. 1. In some implementations, the process 200 can be implemented as computer instructions stored on a computer-readable medium and executable by data processing apparatus. For example, the process 200 can be implemented by the wellbore component life monitoring system 102 of FIG. 1.

At 202, a fatigue model that models the fatigue on a component can be received. For example, the monitoring system 102 can receive a fatigue model from a user of the monitoring system 102. The fatigue model, which can be a mathematical equation, can take a known load configuration of a wellbore component, calculate stress states on the component, and determine an endurance limit for the component based, in part, on the mechanical properties of the component. The equation can be a linear, non-linear, logarithmic, or a combination of them.

In some implementations, a life of a component that the monitoring system 102 determines by executing the fatigue model is a number of cycles at a given load. If the stresses on the component remain under an endurance limit, then the component theoretically can have infinite life. In practice, however, loads on the component are so high that the component cannot have infinite life. The monitoring system 102 can execute the fatigue model based on the stress states and the number of cycles of loads that have been applied to the component to determine a finite life of the component. For example, when a stress state compared to a fatigue limit is provided as an input to the logarithmic equation, the equation can provide as output a number of cycles consumed out of a maximum number of cycles that the component can endure. The output can be reported to an operator as a ratio of the number of cycles to the maximum number of cycles or as a percentage (or both).

A common model for fatigue is combining the stresses using Von Mises into alternating and mean equivalent stresses then applying a fatigue criterion such as Goodman. However, when the alternating and mean stresses are above Goodman, Miner's rule can be applied to determine the number of cycles the component should last.

Von Mises:

$$\sigma_{vm} = \frac{1}{\sqrt{2}}\sqrt{[(\sigma_x - \sigma_y)^2 + (\sigma_y - \sigma_z)^2 + (\sigma_z - \sigma_x)^2 + 6\tau_{xy}^2 + 6\tau_{yz}^2 + 6\tau_{xz}^2]}$$

Goodman:

$$\frac{\sigma_{vm,alternating}}{S_e} + \frac{\sigma_{vm,mean}}{S_u} \leq 1$$

Miner's Rule (Linear Damage Accumulation):

$$C = \sum_{i=1}^{k} \frac{n_i}{N_i}$$

Inverse Weibull Power Law (Advanced Probabilistic Model)

$$f(t) = \beta KS^n (tKS^n)^{\beta-1} e^{-(tks^n)^\beta}$$

At 204, the past history of load values of the loads can be provided as first input to the fatigue model. If the component has not previously been used, then no past history of load values is associated with the component. If the component has previously been used, then the load storage system 120 can store the past history of load values of the loads applied to the component, for example, in a computer-readable storage medium. In response to receiving a request from the monitoring system 102, the load storage system 102 can provide the past history of load values of the loads on the component as the first input to the monitoring system 102, for example, as data transmitted through a wired or wireless network or a mud telemetry system or combinations of them.

If the component is not being operated in the wellbore 112, then the monitoring system 102 can determine a life of the component by providing the current cumulative damage (i.e., the past history of load values of the loads represented by a number of cycles endured by the part and the load states in which the cycles were endured) to the fatigue model, and executing the fatigue model. By doing so, the monitoring system 102 can determine a consumed portion of the life of the component.

At 206, an updated fatigue model can be determined using the past load history. Because the stress state of the component is constantly changing while the load is being applied, the life consumed is also constantly changing. For example, if the component is operated at 10,000 ft.lbs at 200 rpm for 10 hours, the monitoring system 102 can execute the fatigue model to determine that 50% of the component life has been consumed. If the load on the component is decreased to 8,000 ft.lbs at 150 rpm for another 10 hours, then the monitoring system 102 can execute the fatigue model to determine that, e.g., 25% (or less) of the component life has been consumed. If the component is operated under both conditions, for example, in two discrete operations, then the monitoring system 102 can determine that a cumulative, e.g., 75% of the component life has been consumed. The percentages provided here are examples; the relationship need not be linear.

At 208, a check can be performed to determine if the component is still operational. If the component is operational (decision branch "YES"), then, at 210, the load values of the load being applied to the component can be received while the load is being applied to the component. For example, the monitoring system 102 can provide the load values of the load received from the load measuring system 114 while the load is being applied to the component as a second input to the fatigue model.

At 212, the fatigue can be determined from the fatigue model using the load values of the load and the past history. For example, the monitoring system 102 can execute the fatigue model based on the first input and the second input resulting in the fatigue as an output. In other words, the monitoring system 102 can provide the first input and the second input as inputs to the mathematical equation that represents the fatigue model. By executing the fatigue model, the modeling system 102 can obtain a fatigue on the component as a number of cycles of the load applied to the component.

At 214, a comparison of the fatigue that has been determined for the component and a threshold fatigue determined for the component can be performed. The threshold fatigue can be determined, for example, from previous uses of identical or substantially similar components that have been operated under identical or similar field conditions. For example, the threshold fatigue can be represented as a maximum number of cycles that an identical or similar component can endure. The maximum number of cycles can be a statistical representation (e.g., an average) of a predetermined number of identical or substantially similar components.

At 216, a check can be performed to determine if the fatigue has exceeded the threshold fatigue. For example, the monitoring system 102 can store the maximum number of cycles for the component, and compare the periodically determined fatigue with the threshold. If the fatigue has exceeded the threshold fatigue (decision branch "YES"), then, at 218, a notification can be sent. For example, the monitoring system 102 can transmit a notification to an operator of the component notifying the operator that the consumed life of the component has exceeded its expected life. The operator can take necessary action, e.g., cease operations to replace the component.

In some implementations, rather than waiting until the periodically determined fatigue has exceeded the threshold, the monitoring system 102 can send the notification before the consumed life of the component equals or exceeds the expected life. For example, the monitoring system 102 can provide the notification when the number of cycles of the load applied to the component approaches the maximum number of cycles. To do so, in some implementations, the monitoring system 102 can periodically compare a difference between the maximum number of cycles and the determined number of cycles against a threshold difference. When the difference becomes less than the threshold difference, then the monitoring system 102 can provide the notification described above. In some implementations, the monitoring system 102 can provide the notification based on a rate at which the number of cycles approaches the maximum number of cycles.

As an alternative or in addition to providing the notification described above, the monitoring system 102 can determine, from the fatigue, an alternative load applicable to the component to decrease a rate at which a used life of the component approaches a maximum life of the component. For example, the monitoring system 102 can determine the fatigue as the number of cycles endured by the component. Based on the maximum number of cycles predicted for the component, the monitoring system 102 can determine a rate at which the number of cycles endured by the component will approach the maximum number of cycles. The monitoring system 102 can determine alternative load conditions, e.g., decreased loads applied for longer times that can decrease the rate at which the number of cycles endured by the component will approach the maximum number of cycles. The monitoring system 102 can provide the decreased loads, longer times, and the decreased rate to the operator.

In some implementations, the monitoring system 102 can receive the load values of the load from the load measuring system 114 in real time. For example, the load measuring system 114 can be configured such that there is no intentional or substantial delay between a time at which the load measuring system 114 measures a load value and a time at which the load measuring system 114 transmits the load value to the monitoring system 102. In other words, any delay in the transmission of a load value by the load measuring system 114 to the monitoring system 102 is not due to any operation by the load measuring system 114. Instead, the delay may be, for example, due to a bandwidth of a network that carries the load values from the load measuring system 114 to the monitoring system 102.

Similarly, monitoring system 102 can determine a fatigue on the component in real time. For example, the monitoring system 102 can determine a fatigue on the component for each load value received from the load measuring system 114 such that there is no intentional or substantial delay between a time at which the monitoring system 102 receives a load value and a time at which the monitoring system 102 determines the fatigue on the component for the load value.

In some implementations, however, a frequency at which the load measuring system 114 measures the load values can be so high that determining a fatigue for each load value can necessitate intensive operations by the load monitoring system 102. For example, the monitoring system 102 can measure axial, bending and torque loads in real time at a sampling rate of 50 Hz. If the monitoring system 102 received measured data from the load measuring system 114 at this frequency, then a significant portion of the processor and memory capacity of the monitoring system 102 may be consumed to determine and provide the fatigue on the component in real time. In such situations, the monitoring system 102 can be configured to bin and analyze the load values received from the load measuring system 114 to determine loading trends, as described below with reference to FIG. 3.

If the check performed at 214 reveals that the fatigue has not exceeded the threshold fatigue (decision branch "NO"), then, at 218, the loads measured by and received from the load measuring system 114 can be added to the past history, and stored, e.g., in the load storage system 120. The loads can be provided to determine the updated fatigue model, as described above at 206. If the check performed at 208 reveals that the component is no longer operational (decision branch "No"), then, at 220, all load values of the load can be stored, e.g., in the load storage system 120. The load values of the load can be stored in the load storage system 120 even if the check performed at 214 reveals that the fatigue exceeds the threshold fatigue. In addition, the fatigue determined as described above can also be stored. During subsequent uses of the component, e.g., in the wellbore 112 or in a different wellbore, the load values stored at 220 can be provided as the past history of loads applied to the component based, in part, on which the updated fatigue on the component can be determined.

Figure 3:
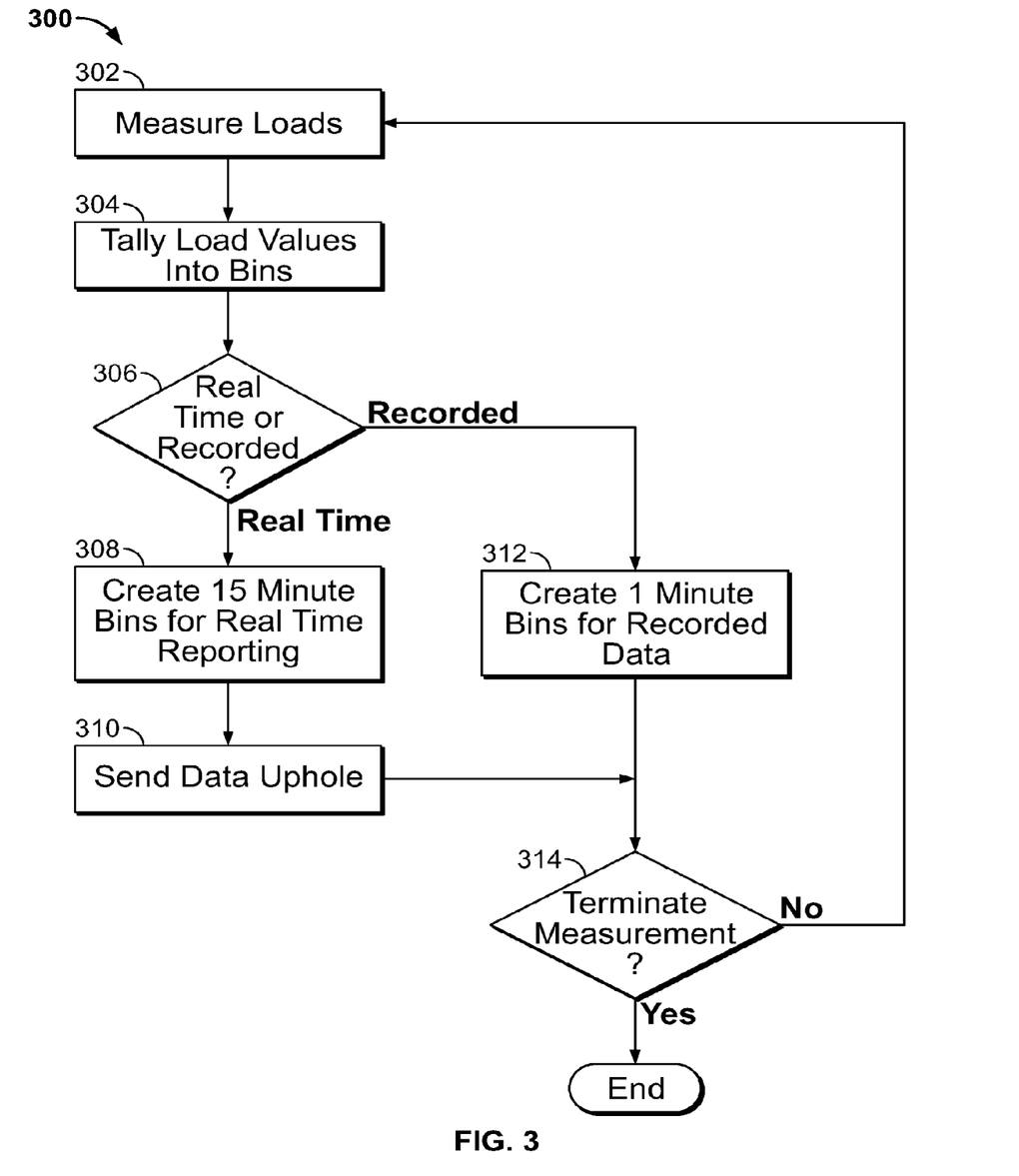
FIG. 3 illustrates a flowchart of an example process for periodically providing load values of loads applied to the component in the wellbore of FIG. 1.

FIG. 3 illustrates a flowchart of an example process 300 for periodically providing load values of loads applied to the component in the wellbore of FIG. 1. In some implementations, the process 300 can be implemented as computer instructions stored on a computer-readable medium and executable by data processing apparatus. For example, the process 300 can be implemented by the load measuring system 114 of FIG. 1.

At 302, the multiple load values of the load can be received at respective multiple sequential time instants. For example, the load measuring system 114 can measure the loads at a frequency, e.g., of 50 Hz. As described above, providing the load values to the monitoring system 102 at the frequency at which the load values are measured can be processor or memory intensive (or both), in part, due to restrictions in bandwidth of the network that carry the load values to the monitoring system 102. Recording the load values at the frequency for providing at a later time may be less processor or memory intensive relative to providing the data in real time. As described below, the load values can be grouped depending on whether the load values are to be provided in real time or recorded.

At 304, the load values can be tallied into bins. For example, the load measuring system 114 can divide the multiple sequential time instants into multiple time segments. Each time segment can include a subset of the multiple sequential time instants. At 306, a check can be performed to determine whether the load values are to be provided in real time or recorded. The duration of a time segment can depend, in part, on whether the load values are to be provided in real time or recorded for subsequent retrieval.

If the load values are to be provided in real time (decision branch "Real Time"), then, at 308, the 15 minute time segments can be created. For each time segment, the load measuring system 114 can identify a subset of the multiple load values received at sequential time instants included in the time segment. The load measuring system 114 can determine a representative load value that statistically represents load values in the subset. For example, the load measuring system 114 can determine an average load value of the load values in the subset.

At 310, the load values can be sent to the surface. For example, the load measuring system 114 can provide the representative value of the subset to the monitoring system 102. By doing so, the load measuring system 114 can provide a representative load value once every 15 minutes, thereby decreasing processor and memory resources relative to providing load values at the frequency at which the load values are measured. The monitoring system 102 can determine the fatigue on the component based on the multiple representative load values determined for the multiple time segments, each representative load value received once every 15 minutes from the load measuring system 114. The 15 minute interval described above is one example of a duration of a time segment. Other durations can be selected based, in part, on available processor or memory capacity, and network bandwidth.

If the load values are to be recorded for providing later (decision branch "Recorded"), then, at 312, the 1 minute segments can be created. For each time segment, the load measuring system 114 can determine a representative load value that statistically represents load values in the subset, as described above. The load measuring system 114 can store the representative load values. These values can be subsequently retrieved, for example, when the component is removed from the wellbore 112. The 1 minute interval described above is one example of a duration of a time segment. Other durations can be selected, e.g., that are less than the duration for the real-time transmission described above. At 314, a check can be performed to determine whether the measurement of loads can be terminated. If the measurement can be terminated (decision branch "YES"), then the process 300 ends. If the measurement cannot be terminated (decision branch "YES"), then the process 300 can be repeated starting at 302. In sum, by implementing the techniques described above, the monitoring system 102 can record cumulative damage on the component, add the cumulative damage to a run history on the component, and update the cumulative damage during the run. By implementing such condition-based maintenance, an operator of the component can replace the component, e.g., when 90% of the component life has been consumed.

Figure 4:
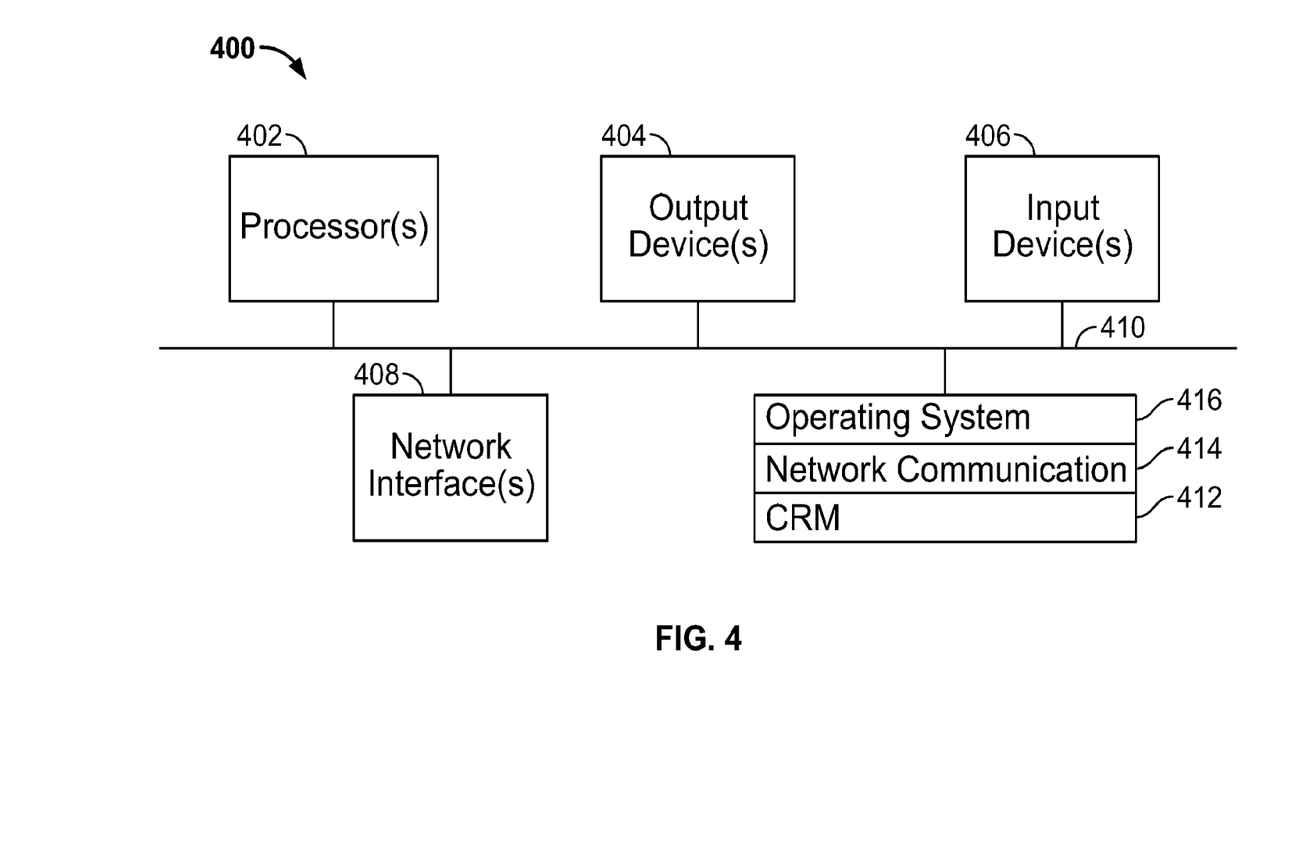
FIG. 4 illustrates an example computer system architecture of the wellbore component life monitoring system of FIG. 1.

FIG. 4 illustrates an example computer system architecture 400 of the wellbore component life monitoring system 102 of FIG. 1. Other architectures are possible, including architectures with more or fewer components. In some implementations, architecture 400 includes one or more processors 402 (e.g., dual-core Intel® Xeon® Processors), one or more output devices 404 (e.g., LCD), one or more network interfaces 408, one or more input devices 406 (e.g., mouse, keyboard, touch-sensitive display, microphone to receive audio input) and one or more computer-readable mediums 412 (e.g., RAM, ROM, SDRAM, hard disk, optical disk, flash memory, etc.) such as the computer-readable medium 106. These components can exchange communications and data over one or more communication channels 410 (e.g., buses), which can utilize various hardware and software for facilitating the transfer of data and control signals between components.

The term "computer-readable medium" refers to a medium that participates in providing instructions to processor 402 (e.g., data processing apparatus 104) for execution, including without limitation, non-volatile media (e.g., optical or magnetic disks), volatile media (e.g., memory) and transmission media. Transmission media includes, without limitation, coaxial cables, copper wire and fiber optics.

Computer-readable medium 412 can further include operating system 416 (e.g., a Linux® operating system) and network communication module 414. Operating system 416 can be one or more of multi-user, multiprocessing, multitasking, multithreading, real time, etc., or combinations of them. Operating system 416 performs basic tasks, including but not limited to: recognizing input from and providing output to devices 404, 806; keeping channel and managing files and directories on computer-readable mediums 412 (e.g., memory or a storage device); controlling peripheral devices; and managing traffic on the one or more communication channels 410. Network communications module 414 includes various components for establishing and maintaining network connections (e.g., software for implementing communication protocols, such as mud telemetry, etc.).

The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result.

A system of one or more computers can be configured to perform particular actions by virtue of having software, firmware, hardware, or a combination of them, installed on the system that in operation causes or cause the system to perform the actions. One or more computer programs can be configured to perform particular actions by virtue of including instructions that, when executed by data processing apparatus, cause the apparatus to perform the actions.

A number of implementations have been described. Nevertheless, it will be understood that various modifications may be made without departing from the spirit and scope of the disclosure. In some implementations, the load measuring system 114 can be configured to determine a fatigue on the component. To do so, the load measuring system 114 can store and execute the fatigue model based on the first input that represents load values of loads presently being applied to the component and the second input that represents the past history received from the load storage system 120. The load measuring system 114 can periodically transmit the determined fatigue to the monitoring system 102. The monitoring system 102 can be configured to receive the fatigue from the load measuring system 114, and provide notifications to an operator of the component as described above.

What is claimed is:

1. A system for monitoring a life of a wellbore tool in a wellbore, the system comprising:
   a sensor positioned in a wellbore, the sensor coupled to the well tool implemented in the wellbore, the sensor configured to sense load values of loads being applied to the well tool during operation of the well tool in the wellbore;
   data processing apparatus coupled to the sensor, the data processing apparatus and the sensor configured to exchange data including the load values of the loads applied to the well tool; and
   a computer-readable medium storing instructions executable by the data processing apparatus to perform operations comprising:
      periodically receiving, from the sensor, the load values of the loads while the loads are being applied to the well tool in the wellbore and while the well tool is operating in the wellbore; and
      while the loads are being applied to the well tool in the wellbore, periodically determining a fatigue on the well tool caused by the loads based, at least in part, on the periodically received load values, and
   wherein periodically determining the fatigue on the well tool comprises:
      periodically determining a number of cycles of the loads applied to the well tool;
      comparing the number of cycles of the loads to a maximum number of cycles that are applicable to the well tool, the number of cycles applied to the well tool increasing over time; and
      outputting a notification when the number of cycles of the load applied to the well tool approaches the maximum number of cycles, wherein downhole failures can be prevented by performing scheduled repairs or replacements based on the notification.

2. The system of claim 1, further comprising periodically receiving the load values of the loads while the well tool is being operated in the wellbore.

3. The system of claim 1, further comprising a load storage system to store a past history of load values of loads that were applied to the well tool, wherein the operations further comprise:
receiving the past history of load values of the loads that were applied to the well tool; and
periodically determining the fatigue caused by the load based on the past history of loads.

4. The system of claim 1, wherein the operations further comprise determining, from the fatigue, an alternative load applicable to the well tool to decrease a rate at which a used life of the well tool approaches a maximum life of the well tool.

5. The system of claim 1, the operations further comprising:
receiving a plurality of load values of the load at respective plurality of sequential time instants; and
periodically determining the fatigue caused by the load on the well tool based, at least in part, on the periodically received plurality of load values by:
dividing the plurality of sequential time instants into a plurality of time segments, each time segment including a subset of the plurality of sequential time instants; and
for each time segment:
identifying a subset of the plurality of load values received at sequential time instants included in the time segment, and
determining a representative load value that statistically represents load values in the subset; and
determining the fatigue on the well tool based on a plurality of representative load values determined for the plurality of time segments.

6. The system of claim 1, further comprising a load measuring system coupled to the sensor to:
periodically measure the load value of the load while the load is being applied to the well tool; and
provide the load value of the load while the load is being applied to the well tool.

7. The system of claim 6, wherein the load measuring system comprises:
a strain gauge to sense a strain on the well tool; and
a computer system coupled to the strain gauge, the computer system configured to:
receive the strain sensed by the strain gauge; and
transform the strain into the load value of the load applied to the well tool.

8. The system of claim 1, wherein periodically receiving the load values comprises receiving the load values in real-time from the sensor.

9. The system of claim 1, wherein well tool comprises at least one of a drill bit to drill the wellbore, a drive shaft, a mud motor, a rotary steerable system or a formation evaluation collar.

10. A system for monitoring a life of a well tool in a wellbore, the system comprising:
a sensor positioned in a wellbore, the sensor coupled to a well tool implemented in the wellbore, the sensor configured to sense load values of loads being applied to the well tool during operation of the well tool in the wellbore;
data processing apparatus coupled to the sensor, the data processing apparatus and the sensor configured to exchange data including the load values of the loads applied to the well tool; and
a computer-readable medium storing instructions executable by the data processing apparatus to perform operations comprising:
periodically receiving, from the sensor, the load values of the loads while the loads are being applied to the well tool in the wellbore and while the well tool is operating in the wellbore; and
while the load is being applied to the well tool in the wellbore, periodically determining a fatigue on the well tool caused by the load based, at least in part, on the periodically received load value, and
wherein periodically determining the fatigue on the well tool caused by the load comprises:
receiving a fatigue model that models the fatigue on the well tool;
providing the past history of load values of the loads as a first input to the fatigue model;
providing the load value of the load while the load is being applied to the well tool as a second input to the fatigue model; and
executing the fatigue model based on the first input and the second input resulting in the fatigue as an output; and
output the fatigue in response to receiving the first input and the second input, wherein downhole failures can be prevented by performing scheduled repairs or replacements based on the fatigue.

11. The system of claim 10, wherein the past history of load values include load values measured during a previous operation of the well tool that is different from an operation of the well tool in which the load is being applied to the well tool.

12. The system of claim 10, wherein the past history of load values include load values measured for each operation in which the well tool was run into and out of the wellbore.

13. The system of claim 10, wherein the past history of load values includes wellbore conditions that were drilled using the well tool.

14. The system of claim 13, wherein the wellbore conditions include types of formations that were drilled using the well tool.

15. A method for monitoring a life of a well tool in a wellbore, the method comprising:
receiving, in real time and from a sensor positioned in a wellbore coupled to a well tool in the wellbore, load values of loads while the load are being applied to the well tool in the wellbore and while the well tool is being operated in the wellbore;
while the load is being applied to the well tool in the wellbore, determining, in real time, a fatigue on the well tool caused by the load based, at least in part, on the received load value;
receiving a fatigue model that models the fatigue on the well tool;
receiving a past history of load values of the loads that were applied to the well tool;
providing the load value of the load while the load is being applied to the well tool as a second input to the fatigue model; and
executing the fatigue model based on the first input and the second input resulting in the fatigue as an output; and outputting the fatigue in response to receiving the first input and the second input, wherein downhole failures can be prevented by performing scheduled repairs or replacements based on the fatigue.

16. The method of claim 15, further comprising determining, from the fatigue, an alternative load applicable to the well tool to decrease a rate at which a used life of the well tool approaches a maximum life of the well tool.

17. The method of claim 15, further comprising:
receiving a plurality of load values of the load at respective plurality of sequential time instants; and
determining the fatigue caused by the load on the well tool based, at least in part, on the received plurality of load values by:
dividing the plurality of sequential time instants into a plurality of time segments, each time segment including a subset of the plurality of sequential time instants; and
for each time segment:
identifying a subset of the plurality of load values received at sequential time instants included in the time segment, and
determining a representative load value that statistically represents load values in the subset; and
determining the fatigue on the well tool based on a plurality of representative load values determined for the plurality of time segments.

18. The method of claim 15, further comprising:
measuring, in real time, the load value of the load while the load is being applied to the well tool by:
sensing a strain on the well tool using a strain gauge, and
transforming the strain into the load value of the load applied to the well tool; and
providing the load value of the load while the load is being applied to the well tool.

19. The method of claim 15, further comprising determining a ratio of the number of cycles to the maximum number of cycles, and wherein providing the notification comprises providing the ratio.

20. A method for monitoring a life of a well tool in a wellbore, the method comprising:
receiving, in real time and from a sensor positioned in a wellbore coupled to a well tool in the wellbore, load values of loads being applied to the well tool during operation of the well tool in the wellbore, wherein the well tool is implemented in and is operating in the wellbore; and
while the load is being applied to the well tool in the wellbore, determining, in real time, a fatigue on the well tool caused by the load based, at least in part, on the received load value, and
wherein determining, in real time, the fatigue on the well tool comprises:
determining, in real time, a number of cycles of the load applied to the well tool;
comparing the number of cycles of the load to a maximum number of cycles that are applicable to the well tool, the number of cycles applied to the well tool increasing over time; and
outputting a notification when the number of cycles of the load applied to the well tool approaches the maximum number of cycles, wherein downhole failures can be prevented by performing scheduled repairs or replacements based on the notification.

21. A non-transitory computer-readable medium storing instructions executable by data processing apparatus to perform operations comprising:
connecting a data processing apparatus configured to execute the instructions stored on the non-transitory computer-readable medium to a sensor positioned in a wellbore, the sensor coupled to a well tool implemented in and operating in the wellbore, the sensor configured to sense load values of loads being applied to the well tool during operation of the well tool in the wellbore;
periodically receiving, at the data processing apparatus and from the sensor, the load values of the loads while the loads are being applied to the well tool in the wellbore and while the well tool is being operated in the wellbore;
receiving, at the data processing apparatus, a past history of load values of loads that were applied to the well tool in previous, separate instances of operation of the well tool; and
while the loads are being applied to the well tool in the wellbore, periodically determining, by the data processing apparatus, a fatigue on the well tool caused by the load based, at least in part, on the periodically received load value and the past history of load values of the loads;
receiving, at the data processing apparatus, a fatigue model that models the fatigue on the well tool;
receiving, at the data processing apparatus, a past history of load values of the loads that were applied to the well tool;
providing, by the data processing apparatus, the load value of the load while the load is being applied to the well tool as a second input to the fatigue model; and
executing, by the data processing apparatus, the fatigue model based on the first input and the second input resulting in the fatigue as an output; and
providing, by the data processing apparatus, the fatigue in response to receiving the first input and the second input, wherein downhole failures can be prevented by performing scheduled repairs or replacements based on the fatigue.

22. The medium of claim 21, the operations further comprising determining, from the fatigue, an alternative load applicable to the well tool to decrease a rate at which a used life of the well tool approaches a maximum life of the well tool.

* * * * *